United States Patent [19]

Nakanishi

[11] 4,021,917
[45] May 10, 1977

[54] DENTAL HANDPIECE AND A CARTRIDGE FOR A HEAD THEREOF

[75] Inventor: Toshimasa Nakanishi, Kanuma, Japan

[73] Assignee: Nakanishi Dental Mfg., Co., Ltd., Kanuma, Japan

[22] Filed: Feb. 20, 1975

[21] Appl. No.: 551,406

[52] U.S. Cl. .................................................. 32/27
[51] Int. Cl.² ......................................... A61C 1/12
[58] Field of Search ........................ 32/27, 26, 58

[56] References Cited

UNITED STATES PATENTS

| | | | |
|---|---|---|---|
| 1,853,089 | 4/1932 | Skinner | 32/27 |
| 3,408,043 | 10/1968 | Williams | 32/27 |

*Primary Examiner*—Robert Peshock
*Attorney, Agent, or Firm*—Armstrong, Nikaido & Marmelstein

[57] ABSTRACT

A dental handpiece of the present invention is provided with a head extending at substantially a right angle to said handpiece having a hollow therein. The head is also provided with a hollow vertically communicating with the hollow of the handpiece. A semispherical groove is cut into the hollow wall longitudinally and partially adjacent an orifice of the head. A cartridge having an elongated opening cut through at a mid-portion of a bottom thereof and also a small opening at a top wall near a lower orifice and at the same position as the semispherical groove is mounted into its hollow with a rotatable bushing through metal bearings inserted into a lower and upper orifices of the hollow. A gear is secured to the bushing at a position to form an entry into the elongated opening of the cartridge. Together with the spherical groove of the head and the small opening of the cartridge, a semispherical cavity cut into the lower metal bearing defines a spherical space for a metal ball. Accordingly, when the cartridge having a reamer is inserted into the head, the metal ball is fitted in a protruding fashion into the semispherical groove to prevent idling between the gear and metal bearings. The gear secured to the bushing can be easily adapted to mesh with a gear of the driving gear rotatably mounted within the handpiece, thus enabling the dentist to easily exchange the cartridge comprising the worn out parts.

2 Claims, 4 Drawing Figures

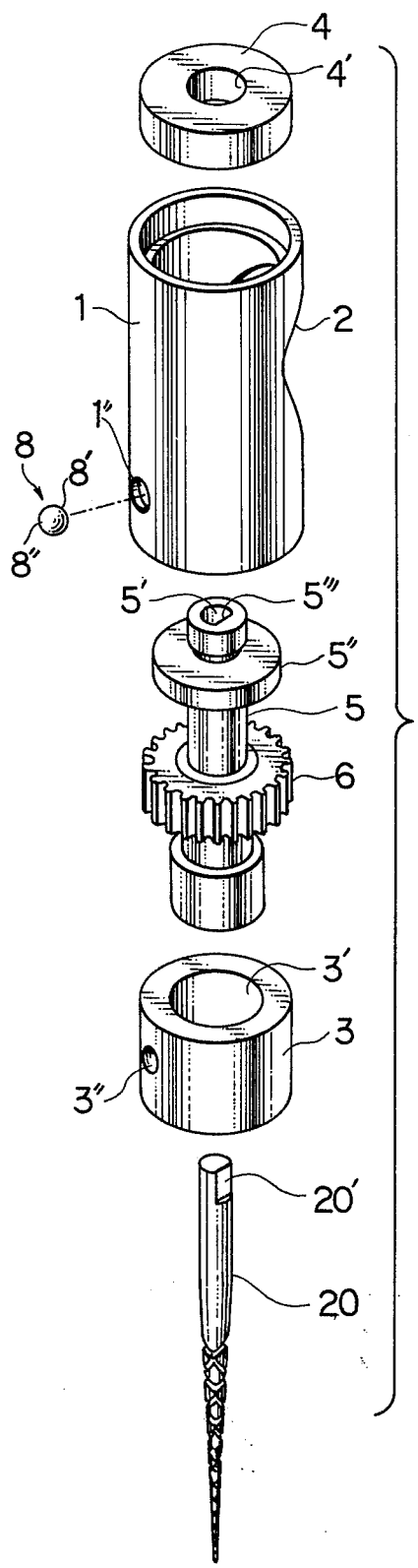
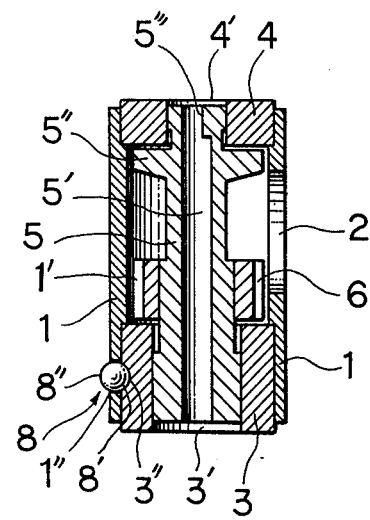

DENTAL HANDPIECE AND A CARTRIDGE FOR A HEAD THEREOF

BRIEF SUMMARY OF THE INVENTION

This invention relates to improvements in a dental handpiece and a cartridge for a head thereof which enables a dentist to easily exchange a cartridge comprising worn out parts and also assuring smooth operation of the dental handpiece.

A dental handpiece becomes unserviceable after a long use when a driving gear secured to a reamer bushing within a head is abraded or metal bearings for said bushing are worn off this causing a backlash. As a practical, matter, it is difficult for a dentist to exchange these abraded or worn out parts within the head for the new ones. It is customary for some dentists to entrust a repairman with its repair or to abandon the dental handpiece entirely.

A principal object of this invention is to provide a motor driven dental handpiece comprising a head, including a cartridge whereby exchange of the cartridge having the abraded or worn out parts such as a gear, metal bearings, etc. can be performed quickly and easily.

Another object of this invention is to provide a cartridge which can be either fixed into or removed from the head of a dental handpiece to insert remove a reamer, a drill on the like easily.

A further object of this invention is to provide a cartridge whereby an idling between the cartridge and metal bearings can be prevented to assure smooth operation of the reamer for the dental handpiece.

A still further object of this invention is to provide a device which will enable the dentist to exchange the abraded parts within the head for new ones in a simpler and faster method and with ease of operation.

BRIEF DESCRIPTION OF DRAWINGS

While I have shown in the accompanying drawings, a preferred embodiment of my invention, it should be understood that the same is susceptible of modification and change without departing from the spirit of my invention.

Referring to the drawings.

FIG. 3 is an enlarged perspective view of the disassembled parts which are adapted to be inserted into the head of the dental handpiece to fix the reamer; and FIG. 4 is an enlarged vertical section of the cartridge incliding a bushing therein.

DETAILED DESCRIPTION

Figure 1:
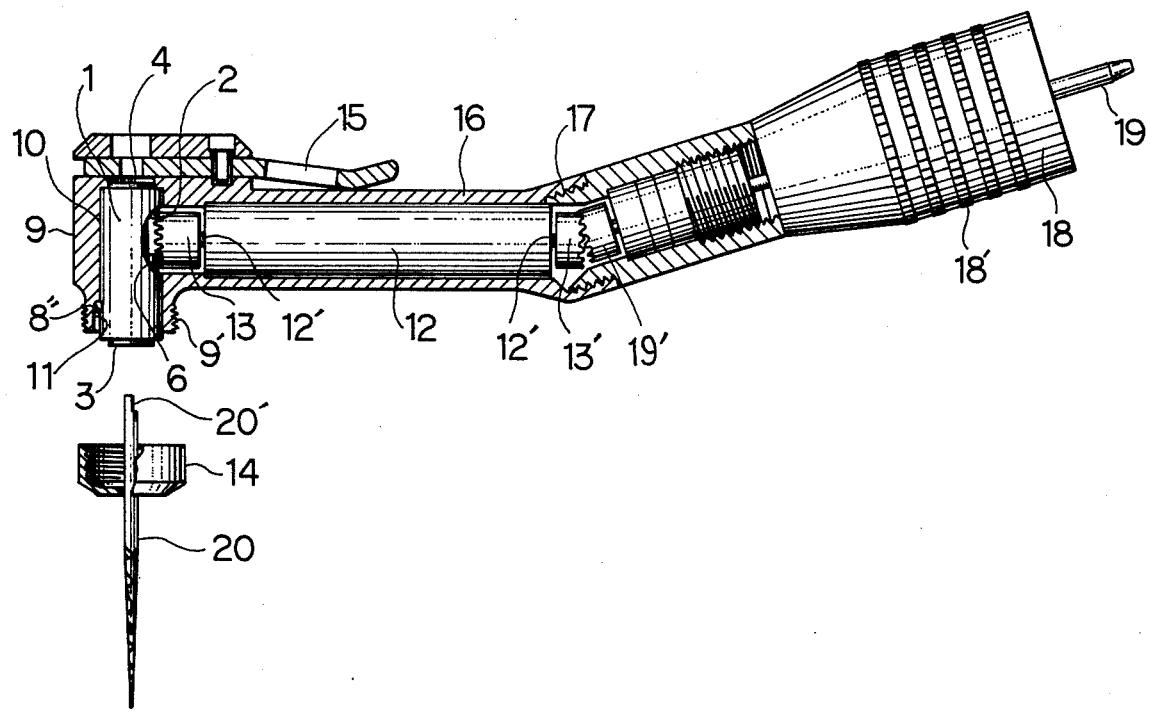
FIG. 1 is an enlarged elevation, partly in section, of a dental handpiece for a motor driven reamer, showing particularly a head, a cartridge, a driving shaft, a cap and the reamer.
Figure 2:
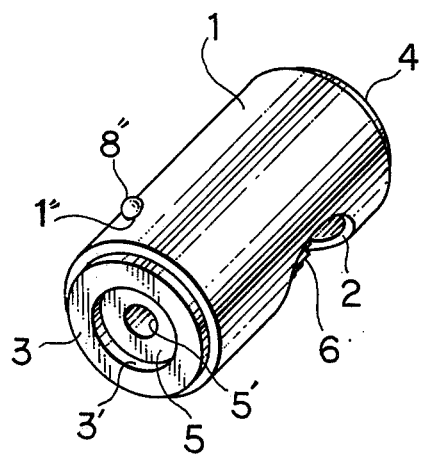
FIG. 2 is an enlarged perspective view of the cartridge to be inserted into the head.

A preferred embodiment which has been selected to illustrated the present invention comprises a dental handpiece 16 which includes at its one end a head 9 extending at substantially a right angle to said dental handpiece. The head 9 is provided with a hollow 10 vertically communicating with a hollow of said handpiece, a semispherical groove 11 is cut into the hollow wall longitudinally and partially adjacent an orifice of said head, and a screw thread 9' is provided around and adjacent the orifice thereof.

A cartridge 1 is provided with an elongated opening 2 at about the midportion of the wall thereof, and a small opening 1" is provided through the wall of the cartridge 1 near its lower orifice. A semispherical cavity 3" is cut into a portion of a metal bearing 3, which position can correspond to the small opening 1" when the metal bearing 3 is inserted into a hollow 1' of the cartridge 1.

A stopper 5' is provided to a bushing 5 near an upper end thereof. An end portion of a hollow wall 5 adjacent the upper orifice of said bushing is partially protruded to form a flat stopper 5''' for a reamer 20. Secured to the bushing 5 is a gear 6 at a position that said gear may open out into the elongated opening 2 of the cartridge 1 so as to permit the driven gear 6 to engage with a driving gear 13 of a shaft 12' through the elongated opening 2. The bushing 5 is rotatably mounted into the hollow 1' of the cartridge 1 through the metal bearings 3 and 4 in their lower and upper orifices respectively so that the semispherical cavity 3" may coincide with the small opening 1" of the cartridge, thus defining a spherical space for a metal ball 8. Then, a lower semisphere 8' of the metal ball 8 is inserted into the cavity 3", while an upper semisphere 8" is protruded through and beyond the small opening 1" to fit into the semispherical groove 11 so that an idling between the cartridge 1 and metal bearings 3 and 4 can be prevented.

The reamer 20 having a depressed portion 20' on a side adjacent the top end thereof is inserted into the hollow 5' of the bushing 5 to fit the depressed stage 20' into the stopper 5''', and a cap 14 is threadedly mounted onto the screw thread 9' of the head 9 so as to secure the reamer 20.

The driving shaft 12' rotatably mounted in an intermediate bushing 12 is provided with a gear 13 at its one end and also with another gear 13° at its other end respectively, while the bushing 12 is securely mounted within the dental handpiece 16 in such a way that the gear 13 may locate in a position to an inner orifice of said handpiece to engage with the gear 6 through the elongated opening so as to transfer rotation to the reamer 20, and the gear 13' may locate in a position adjacent to a screw thread 17 of another orifice of the bent end portion of the bushing 12.

A gear 19' is secured in an inner end of the driving shaft 19 which is rotatably mounted in a bushing mounted which in turn is in tube 18 provided in parallel are a plurality of nicks 18' around the coupling tube 18 to form an anti-skid grip. The shaft 19 is coupled to a motor (not shown). A molding fixing metal 15 is provided on a top portion of the head 9 and handpiece 16.

Upon assembling, the cartridge 1 is inserted into the hollow 10 of the head 9 so that the upper semisphere 8" of the metal ball 8 is protruded into the semispherical groove 11 and the lower semisphere 8' is fitted into the cavity 3" to arrest an idling between the cartridge 1 and bearingss 3 and 4. Accordingly, the driven gear 6 is adapted to be in mesh with the driving gear 13 of the shaft 12' rotatably mounted within the intermediate bushing 12, which is securely enclosed in the handpiece 16.

When it becomes necessary to exchange the cartridge 1 comprising the worn out gear 6, metal bearings 3 and 4, the coupling tube 18 is first unscrewed from the dental handpiece 16, the intermediate bushing 12 is pulled out of said handpiece, the cap 14 is also unscrewed, then the cartridge 1 can be readily pulled out of the hollow 10 of the head 9. As a consequence, the new cartridge 1 comprising completely gear 6, and metal bearings 3 and 4 can be inserted easily and immediately into the hollow 10 of the head 9.

The use of the present dental handpiece and cartridge enables the dentist to repair or exchage the abraded or worn out parts within the cartridge in much less time than has previously been possible by exchanging said cartridge for a new one, while also lengthening the life of the dental handpiece and assuring complete operation thereof.

From the foregoing, it is believed that the features and advantages of my invention will be readily apparent to those skilled in the art and it will be understood that changes in the form, proportion and minor details of construction may be resorted to without departing from the spirit or the scope of the appended claims.

I claim:

1. A dental handpiece comprising a head at one end and an engaging screw thread at another end, said head extending at substantially a right angle to said handpiece, said engaging screw thread being disposed around a wall adjacent a partially bent end portion of said handpiece, said head being provided with a hollow vertically communicating with a hollow of said handpiece, a semispherical groove cut in the wall longitudinally and partially adjacent an orifice of said head, and a screw thread provided around and adjacent said orifice, respectively, a driving shaft rotatably mounted in an intermediate bushing which is adapted to be securely disposed within the dental handpiece, said driving shaft being provided with gears at each end, one gear being located adjacent an inner orifice communicating with the hollow of the head and another gear being located adjacent an outer orifice of the handpiece, said engaging screw thread of the handpiece being adapted to connect to a coupling tube, a cartridge which is adapted for insertion into the hollow of the head so as to secure a reamer into said head, said cartridge having an elongated opening cut through the wall thereof at its midportion and a small opening provided through the wall thereof near an lower orifice thereof adapted to correspond to the semispherical groove, said cartridge including two metal bearings securely disposed in the lower and upper orifices respectively, said lower metal bearing being provided with a semispherical cavity at a portion corresponding to the small opening of the cartridge, a bushing rotatably inserted into the cartridge through these metal bearings, said bushing having a stopper near an upper end thereof and a gear secure at a position that said gear is adapted to open out into the elongated opening of the cartridge for permitting the driven gear of the bushing to engage with the driving gear of the driving shaft through the elongated opening of the cartridge, and an end portion of a wall adjacent the upper orifice of said bushing being partially projected to form a flat stopper for securing a reamer.

2. A dental handpiece according to claim 1, wherein a metal ball is inserted into a spherical space defined by the semispherical cavity of the lower metal bearing, the small opening of the cartridge and the semispherical groove of the head so as to prevent idling between the cartridge and metal bearings when the bushing is disposed into the cartridge, a depressed portion on a side adjacent a top end of the reamer is adapted to fit onto the flat stopper within the hollow of the bushing, and a cap screw threadedly mounted onto the screw thread of the head to secure the reamer.

* * * * *

UNITED STATES PATENT OFFICE
CERTIFICATE OF CORRECTION

Patent No. 4,021,917  Dated May 10, 1977

Inventor(s) Toshimasa Nakanishi

It is certified that error appears in the above-identified patent and that said Letters Patent are hereby corrected as shown below:

Column 1, line 14, change "this" to --, thus --;

lines 14 and 15, change "practical, matter" to -- practical matter --;

line 28, after "insert" insert -- or --;

line 29, change "on" to -- or --'

Column 2, line 37, change "13°" to -- 13' --;

line 48, after "in" insert -- a coupling --;

after "18" insert -- . --;

Column 3, line 2, after "completely" insert -- new --;

after "6" delete --,--.

Signed and Sealed this

Twenty-seventh Day of September 1977

[SEAL]

Attest:

RUTH C. MASON  
Attesting Officer

LUTRELLE F. PARKER  
Acting Commissioner of Patents and Trademark

UNITED STATES PATENT OFFICE
CERTIFICATE OF CORRECTION

Patent No. 4,021,917             Dated May 10, 1977

Inventor(s) Toshimasa Nakanishi

It is certified that error appears in the above-identified patent and that said Letters Patent are hereby corrected as shown below:

Column 2, line 48, change "provided" to --Provided--

Signed and Sealed this

Eleventh Day of April 1978

[SEAL]

Attest:

RUTH C. MASON
Attesting Officer

LUTRELLE F. PARKER
Acting Commissioner of Patents and Trademarks